United States Patent [19]
Dunn

[11] Patent Number: 5,274,500
[45] Date of Patent: Dec. 28, 1993

[54] VIDEO CAMERA DRAPE WITH LENS

[75] Inventor: James L. Dunn, Topeka, Kans.

[73] Assignee: Kansas City Medical, Inc., Olathe, Kans.

[21] Appl. No.: 919,181

[22] Filed: Jul. 23, 1992

[51] Int. Cl.$^5$ .................. G03B 11/04; B65D 85/38
[52] U.S. Cl. .................... 359/507; 359/510; 359/900; 206/316.1
[58] Field of Search .......... 359/507, 510–512, 359/900; 128/4, 6, 846–849; 358/98, 229; 206/316.1–361.13, 438, 369, 63.5, 69

[56] References Cited

U.S. PATENT DOCUMENTS

| | | | |
|---|---|---|---|
| 3,528,720 | 9/1970 | Treace | 359/510 |
| 3,698,791 | 10/1972 | Walchle et al. | 359/510 |
| 3,794,091 | 2/1974 | Ersek et al. | 150/154 |
| 4,522,196 | 6/1985 | Cunningham et al. | 128/4 |
| 4,561,540 | 12/1985 | Hunter et al. | 359/510 |
| 4,615,331 | 10/1986 | Kramann | 128/4 |
| 4,799,779 | 1/1989 | Mesmer | 359/510 |
| 4,854,302 | 8/1989 | Allred, III | 358/98 |
| 4,878,485 | 11/1989 | Adair | 128/6 |
| 4,914,521 | 4/1990 | Adair | 358/229 |
| 4,979,498 | 12/1990 | Oneda et al. | 128/6 |
| 5,010,876 | 4/1991 | Henley et al. | 128/6 |
| 5,078,483 | 1/1992 | Herzberg | 359/510 |
| 5,122,904 | 6/1992 | Fujiwara et al. | 359/510 |

FOREIGN PATENT DOCUMENTS 8711189  12/1987  Fed. Rep. of Germany.

Primary Examiner—Bruce Y. Arnold
Assistant Examiner—Thong Nguyen
Attorney, Agent, or Firm—Litman, McMahon & Brown

[57] ABSTRACT

The present invention is broadly concerned with an improved surgical drape for an endoscopic video camera device which provides a sealed, sterile encasement of the camera and its associated transmission cable and which permits quick, easy interchanging of various endoscopic rod lenses without contamination of the camera head or cable or distortion of the camera image. More particularly, it is concerned with a drape having an opening for insertion of a camera and cable, a clear lens, and structure for constricting the drape around the camera and cable.

17 Claims, 2 Drawing Sheets

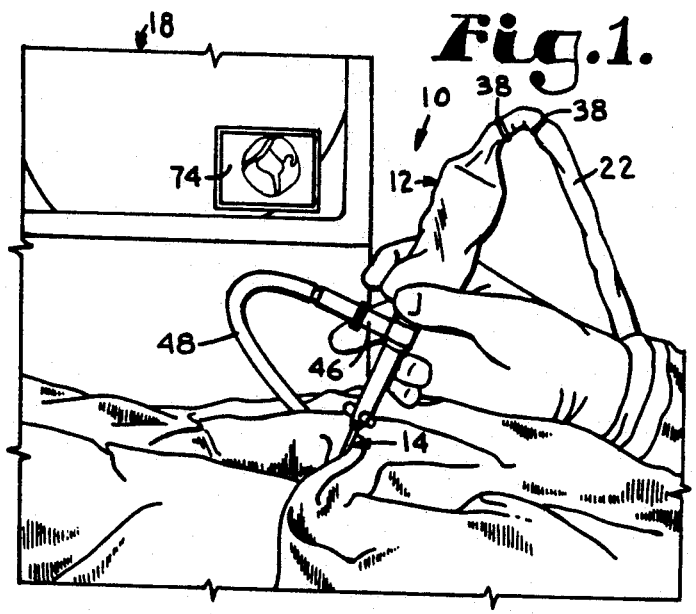
Fig.1.
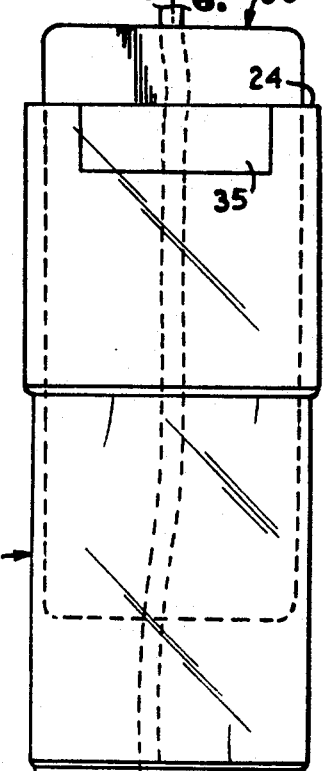
Fig.2.
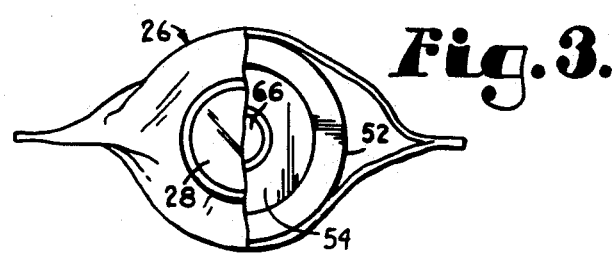
Fig.3.
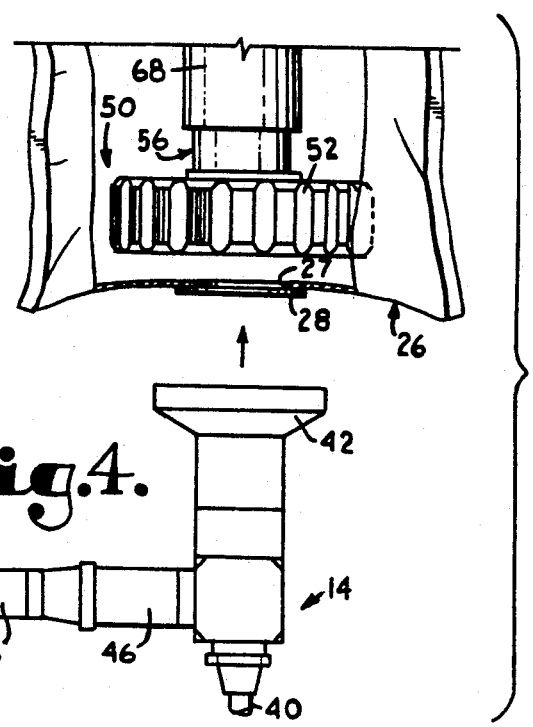
Fig.4.
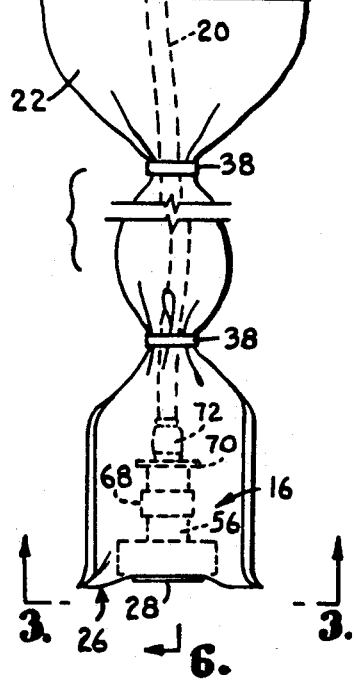

VIDEO CAMERA DRAPE WITH LENS

BACKGROUND OF THE INVENTION

1. Field of the Invention

The present invention is broadly concerned with an improved surgical drape for an endoscopic video camera device which provides a sealed, sterile encasement of the camera and its associated transmission cable and which permits quick, easy interchanging of various endoscopic rod lenses without contamination by the camera head or cable or distortion of the camera image. More particularly, it is concerned with a drape having an opening for insertion of a camera and cable, a clear lens, and structure for constricting the drape around the camera and cable.

2. Description of the Prior Art

Medical examination of the interior of the body and associated therapeutic procedures are now commonly accomplished by video endoscopy. This technique employs a video camera system coupled with an endoscopic telescope to relay images of the interior of the body for projection on a remote video monitor. In practice, a telescope is inserted through a small incision into a joint or cavity portion of the body. Because the telescope has a narrow diameter, surgical trauma to the tissue is minimized, as well as postoperative morbidity and associated extended immobilization and required rehabilitation of the patient.

Use of a video camera head coupled to the telescope permits clear visualization by members of the surgical team and attachment of video recorders for recording of the procedure. However, the camera head is a delicate instrument which may be damaged by conventional sterilization methods such as autoclaving. While cold sterilizable camera heads are available, they are costly and may not be sterilized by the autoclave method which is recommended for destruction certain viruses, including HIV.

Previous surgical drapes for video endoscopic procedures have consisted of conventional drapes in which a hole is made to accommodate the telescope. The telescope may be sterilized, however it must be coupled with the non-sterile camera head to provide a viewing image. In conventional methods, a telescope coupled with the camera head is inserted through a hole in the drape and the drape is attached to the telescope by taping. The body of the drape is swathed around the camera cable. Such installation is time consuming and the drape employed in this manner is bulky, cumbersome, and may partially occlude the surgical field during necessary movement of the camera.

Because the surgical field is wet from blood, body fluids, and fluids such as saline employed to irrigate or distend the body cavity under examination, the tape frequently fails, permitting contamination of the camera head. Once contaminated, the surgical staff as well as subsequent patients are at risk from cross contamination. Moreover, the camera is typically provided with multiple grooves and apertures to enhance gripping by gloved hands, and is consequently extremely difficult to decontaminate.

Moreover, even if the makeshift drape does not fail, it does not permit the telescope to be changed on the sterile field. Since viewing endoscopes are generally fixed focused, e.g. at viewing angles of 0°, 30°, 70°, the camera head must be installed on a new telescope in order to change the surgeon's angle of view. Under conventional methods this would require installation of a new drape, thus extending the duration of the procedure, the anesthesia of the patient, and increasing the possibility of patient morbidity. In addition, since several telescopes and new drapes may commonly be required in a single procedure, the cost of surgical supplies would be increased.

SUMMARY OF THE INVENTION

The present invention overcomes the problems described above and provides a greatly improved sterile drape for a video camera having an attached transmission cable. The drape provides a water and airtight sterile seal which prevents contamination of the camera and its cable while permitting interchanging of telescopes without changing the video camera drape.

The drape in accordance with the present invention broadly includes an elongated tubular member having an open end for insertion of the camera and cable and a closed end having an integral lens for interposition between the rod lens telescope and the camera lens.

Additional embodiments provide removable supports adjacent the open end for supporting the tubular drape in a telescoped fashion and forming an insertion canal for the camera and cable. A constricting means is also provided for constricting the tubular drape around the camera cable.

OBJECTS AND ADVANTAGES OF THE INVENTION

The principal objects and advantages of the present invention include: providing a video camera drape with a lens and method; providing such a drape and method including a water and air tight seal which does not require taping; providing such a drape and method for use with a remote surgical visualization system having a rod lens assembly; providing such a drape and method which permit interchanging of the rod lens assembly without changing the drape; providing such a drape and method including a rigid, optically clear lens which does not distort the camera image; providing such a drape and method including removable support means for supporting the drape in telescoped relationship and forming a canal for quick, easy insertion of a video camera; providing such a drape and method including means for constricting the drape around the cable of a video camera for reducing bulk and permitting easy manipulation of the camera and attached cable; providing such a drape and method for use in combination with existing video endoscopic equipment on hand.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a side elevational view of a video camera drape with lens and constricting means in accordance with the present invention;

FIG. 2 is a side elevational view with support means depicted supporting the tubular member in telescoped relationship, and with a camera head coupled with a cable shown in phantom;

FIG. 3 is a bottom plan view of FIG. 2 with parts broken away to show the lens of the camera head;

FIG. 4 is a partial side elevational view of the draped camera head and endoscope with parts broken away;

DETAILED DESCRIPTION OF THE INVENTION

Figure 5:
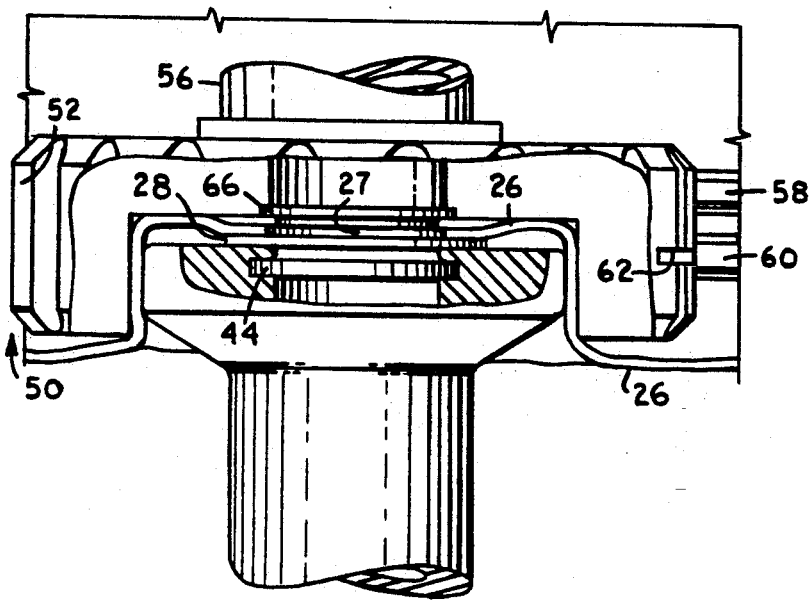
FIG. 5 is an enlarged partial side elevation view of the camera head of a remote surgical visualization system with parts broken away.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring now to the drawing, a remote surgical visualization system 10, which is the functional application for a video camera drape with lens 12 in accordance with the invention, broadly includes a rod lens assembly 14, camera head assembly 16 (best shown in FIG. 2), video display device 18, and intercoupling cable 20. Drape 12 broadly includes tubular member 22 having an open end 24, an opposed closed end 26, including an aperture 27 (best shown in FIG. 5) sealed in covering relationship by lens 28.

In more detail, drape 12 is of flexible tubular construction which may be folded into a flat, telescoped conformation. It is preferably formed of a lightweight, disposable, transparent or translucent synthetic resin material which is obtained in sterile condition from the manufacturer. Alternatively, an unsterile drape may be sterilized according to conventional methods prior to use. Lens 28 is preferably of optically clear, rigid synthetic resin construction such as polycarbonate, polyvinyl chloride, or polypropylene.

As shown in FIGS. 2, 6, 7, and 8, drape 12 may also include a removable flattened, support member 30 adjacent open end 24. In such embodiments, tubular member 22 further includes an inner attachment area 35 adjacent open end 24 and preferably covered with an adhesive substance for attachment of support 30. Support 30 is preferably formed of a pair of opposed flat, semirigid rectangular members 32, 34 which may be transversely compressed while in place in the drape to form an insertion canal 36 within tubular member 22. Those skilled in the art will appreciate that support 30 may also be of unitary construction, longitudinally scored or otherwise formed so as to lie flat. They may be formed of compressed paper such as cardboard, synthetic resin, or any other suitable material.

Figure 6:
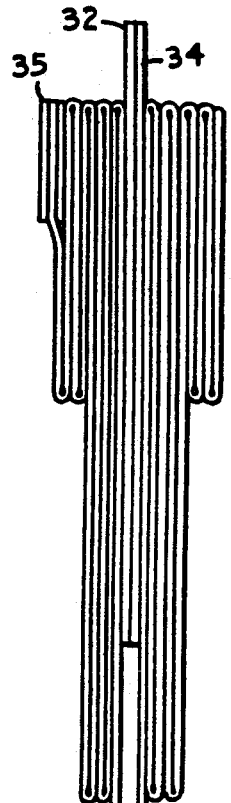
FIG. 6 is a cross section taken along line 6—6 of FIG. 2 with phantom parts omitted.

As shown in FIGS. 1 and 6, drape 12 may also include one or more constriction devices 38, which may be in the form of elastic bands, adhesive or interlocking fabric tabs, or any other easily fastenable construction.

Remote visualization system 10, as depicted in FIGS. 1-5, includes a rod lens assembly 14 having a guide sheath 40 of elongated, rigid tubular metal construction presenting an internal channel in order to accommodate a lens therein. Guide sheath 40 includes an insertion end (not shown) and a flange 42 at the opposed end for mechanical coupling with camera head assembly 16. A lens cover 44 seals the internal channel against contamination. An illumination port 46 is transversely connected to the rod lens assembly adjacent the flanged end and is coupled with an illumination cable 48 which, in turn, is remotely coupled with a light source.

Guide sheath 40 may be of any dimensions, but typically measures from about 2 mm to about 15 mm, being designed for insertion into the body of a patient with a minimum of tissue trauma. The preferred rod lens assembly 14 is a viewing endoscope, such as an arthroscope, having a rigid guide sheath with a single, undivided lumen to accommodate a conventional, fixed angle lens. Those skilled in the art will appreciate that other forms of endoscopic instruments could be employed having flexible guide sheaths employing fiber optic lenses and including various channels coupled with access ports for the passage of fluids, instruments, or vacuum suction therethrough.

Camera head assembly 16 is of conventional construction and is shown in FIGS. 2, 4, and 5 to include a connection collar 50 including an outer sleeve 52, an inner socket 54, transversely coupled with a barrel 56. Outer sleeve 52 is grooved to permit easy grasping by gloved hands and includes a pair of finger pieces 58, 60, one of which is slidable along a transverse groove 62 towards the other. Finger pieces 58, 60 are coupled with spring biased flanges not shown extending axially from the walls of inner socket 54 to facilitate adjustable gripping of rod lens assembly flanges of various sizes in mating relationship. A lens cover 66 seals barrel 56 against contamination. Barrel 56 includes a rotatable focusing knob 68 (best shown in FIG. 2), an objective lens 70, and an image transmission cable port 72.

Cable 20 remotely intercouples cable port 72 and video display device 18 depicted in FIG. 1 with video inset 74. Device 18 may be a cathode ray tube (CRT) or liquid crystal display (LCD). Accessories such as a video recorder may be remotely coupled with visualization system 10 as well.

In use, camera head cable port is remotely coupled with video display device 18 by means of connecting cable 20. Non-sterile camera head assembly 16 is then inserted into open end 24 of the sterile drape and urged forward until inner socket 54 faces drape lens 28 and non-sterile cable 20 projects outwardly from open end 24. Drape lens 28 is next aligned over lens cover 66 and constricting bands 38 fastened at spaced intervals around cable 20 to hold the drape in place. The combination of the tubular configuration of member 22 and constricting bands 38 result in a drape which is not baggy or cumbersome and does not unnecessarily occlude the surgical field.

Figure 7:
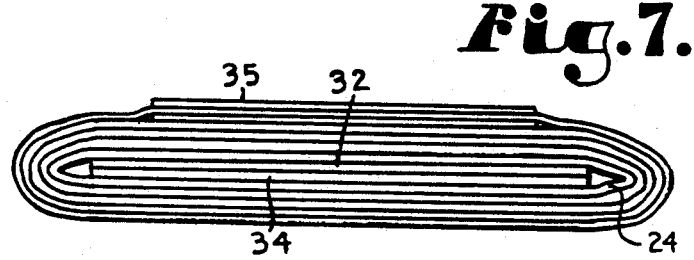
FIG. 7 is a top plan view of the drape of FIG. 6 rotated 90°.
Figure 8:
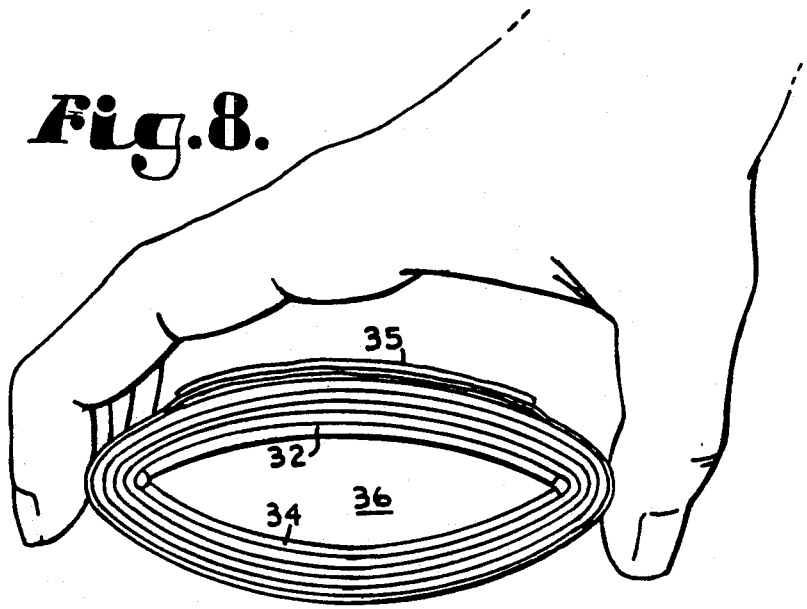
FIG. 8 depicts the drape of FIG. 7 with the ends of the support means compressed to form a camera insertion canal.

As shown in FIGS. 6-8, in certain embodiments, drape 12 is provided with support members 30, installed adjacent the open end 24. Drape 12 is folded over the support members in telescopic manner. Compression of the transverse ends of support members 30 causes formation of a rigid insertion canal 36, which greatly facilitates insertion of the camera. In cases where draping must occur during surgery, this beneficially results in decreased draping time.

As illustrated in FIG. 1, the insertion end of a sterile rod lens assembly 14 such as an endoscope is inserted through an incision and into a joint area or body cavity of a patient. A light source is remotely coupled to illumination port 46 by means of sterile illumination cable 48.

The sterile drape-encased camera head finger pieces 58, 60 are grasped by the fingers and slidable piece 60 is urged along groove 62 toward piece 58. This action causes retraction of attached flange members not shown into the walls of inner socket 54 until the maximum open adjustment of connection collar 50 is achieved. Connection collar 50 is then installed in mating engagement over endoscope flange 42 with camera lens 70, drape lens 28 and endoscope lens cover 44 in alignment. Release of finger pieces 58, 60 results in constriction of the attached spring-biased flange members to lock flange 42 in place, with drape lens 28 sandwiched between camera lens 70 and lens cover 44. Because drape lens 28 is rigid and clear, there is no resulting distortion of the camera image as displayed on video device 18.

Advantageously, the joint area or body cavity may be viewed through a different portal or a through the same portal with a different fixed angle lens by uncoupling camera head assembly 16 from endoscope and recoupling camera 16 with an endoscope in a different portal, while leaving the original endoscope in place for subsequent reviewing. Alternatively, a new sterile endoscope may be inserted in the same portal and coupled with camera 16 following the procedure previously described. Because the drape forms a sterile, water and air-tight encasement which completely seals the non-sterile camera 16 and cable 20 from contact with the sterile endoscope without taping or other means subject to failure, the procedure may be repeated any number of times. In this manner different viewing angles of the joint area or body cavity may be obtained without compromising the sterility of the field or the requiring a change of the drape each time a new endoscope is employed. Since a new sterile drape 12 is employed for each surgical procedure, there is no risk of cross contamination of subsequent patients from the non-sterile camera. Similarly, because the camera is completely encased, there is no risk of cross contamination of surgical or other hospital personnel who may handle the camera following its use in surgery.

The present invention is especially adapted for use with existing endoscopic surgical equipment, such as cameras and their associated cables which may not be sterilized. It may also be employed with newer cameras which may be cold sterilized in cases where heat sterilization is preferable because of the presence of infection.

It is to be understood that while certain forms of the present invention have been illustrated and described herein, it is not to be limited to the specific forms or arrangement of parts described and shown.

The following is claimed as new and desired to be secured by Letters Patent:

1. A drape for a lens assembly including first and second lens portions which are selectively optically linked, said second lens portion having a cable extending therefrom, comprising a tubular drape member having an elongate body, an open end and a closed end, said closed end including an integral drape lens for interposition between said first lens and said second lens portions with said drape in a covering position in covering relationship over said second lens portion and said cable, wherein said drape further includes removable support means inwardly adjacent said open end for supporting said tubular drape member body in telescoped relationship over said support means and forming an insertion canal for said second lens portion.

2. The apparatus as set forth in claim 1, wherein said drape lens is formed of an optically clear material.

3. The apparatus as set forth in claim 2, wherein said drape lens is formed of rigid material.

4. The apparatus as set forth in claim 1, wherein said support means comprises a pair of elongate rectangular support members.

5. The apparatus as set forth in claim 1, wherein said drape further includes means for constricting said tubular drape member around said cable.

6. The apparatus as set forth in claim 5, wherein said constricting means comprises an elastic band in coaxial relationship with said tubular member.

7. In combination with a remote surgical visualization system having a rod lens assembly for insertion into the body of a patient coupled in mating engagement with a camera lens assembly including a lens portion, a video display device, and a cable member remotely intercoupling said camera lens assembly and said video display device, the improvement comprising a tubular drape member covering said camera lens assembly and said cable member for preventing septic contact of said camera lens assembly and said cable member, said drape having an elongate body, an open end and a closed end, said closed end including an integral lens having a position interposed between said matingly engaged rod lens assembly and said camera lens assembly.

8. The apparatus as set forth in claim 7, wherein said drape further includes removable support means inwardly adjacent said open end for supporting said tubular drape member in telescoped relationship over said support means and forming an insertion canal for said camera.

9. The apparatus as set forth in claim 8, wherein said support means comprises a pair of elongate rectangular support members.

10. The apparatus as set forth in claim 7, wherein said drape further includes means for constricting said tubular member around said cable member.

11. The apparatus as set forth in claim 10, wherein said constricting means comprises an elastic band in coaxial relationship with said tubular member.

12. The apparatus as set forth in claim 7, wherein said drape further includes:
  (a) removable support means inwardly adjacent said open end for supporting said tubular drape member body in telescoped relationship over said support means and forming an insertion canal for said camera lens assembly; and
  (b) elastic constricting means in coaxial encircling relationship with said tubular drape member and said support means for constricting said tubular member around said cable member upon removal of said support means.

13. A method of draping a remote surgical visualization system having a rod lens, a camera including a lens portion, a video display, and a cable member remotely intercoupling said camera and said display, for preventing septic contact of said camera and said cable when a drape is placed in covering relationship over said camera and said cable, comprising the steps of:
  (a) providing a tubular drape member having an elongate body, an open end and a closed end, said closed end including an integral drape lens;

(b) inserting said camera into said tubular drape member through said open end and juxtaposing said camera lens portion against said drape lens while permitting said cable member to extend outwardly from said open end; and (c) coupling said rod lens with said camera lens portion while interposing said drape lens therebetween.

14. The method as set forth in claim 13, further including the step of:

(d) providing removable support means inwardly adjacent said open end for supporting said tubular member body in telescoped relationship over said support means and forming an insertion canal for said camera.

15. The method as set forth in claim 13, further including the steps of:

(d) providing means for constricting said tubular member around said camera cable; and (e) constricting said tubular member around said cable.

16. The method as set forth in claim 13, further including the steps of:

(d) providing removable support means inwardly adjacent said open end for supporting said tubular member in telescoped relationship over said support means and forming an insertion canal for said camera;

(e) providing elastic constricting means in coaxial encircling relationship over said tubular member body and said support means; and (f) removing said support means and permitting constriction of said elastic constricting means around said cable member.

17. A method of draping a remote surgical visualization system having first and second rod lens assemblies, a camera lens assembly including a lens portion, a video display, and a cable member remotely intercoupling said camera lens assembly and said display, for preventing septic contact of said camera lens assembly and said cable member when a drape is placed in covering relationship over said camera lens assembly and said cable member, comprising the steps of:

(a) providing an elongate tubular drape member having an open end and a closed end, said closed end including an integral drape lens;

(b) inserting said camera lens assembly into said tubular member through said open end and juxtaposing said camera lens portion against said drape lens while permitting said cable member to extend outwardly from said open end;

(c) coupling said first rod lens assembly with said camera lens portion while interposing said drape lens therebetween; and (d) uncoupling said first rod lens assembly from said camera lens portion and coupling said second rod lens assembly with said camera lens portion while interposing said drape lens therebetween.

* * * * *